(12) United States Patent
Mirizzi et al.

(10) Patent No.: US 8,772,279 B2
(45) Date of Patent: Jul. 8, 2014

(54) 6,7-DIHYDROIMIDAZO[1,5-A]PYRAZIN-8(5H)-ONE DERIVATIVES AS PROTEIN KINASE MODULATORS

(75) Inventors: Danilo Mirizzi, Nerviano (IT); Sten Christian Orrenius, Nerviano (IT); Paolo Trifirò, Como (IT)

(73) Assignee: Nerviano Medical Sciences S.R.L., Nerviano (MI) (IT)

( * ) Notice: Subject to any disclaimer, the term of this patent is extended or adjusted under 35 U.S.C. 154(b) by 0 days.

(21) Appl. No.: 13/575,181

(22) PCT Filed: Jan. 21, 2011

(86) PCT No.: PCT/EP2011/050846
§ 371 (c)(1),
(2), (4) Date: Sep. 5, 2012

(87) PCT Pub. No.: WO2011/092120
PCT Pub. Date: Aug. 4, 2011

(65) Prior Publication Data
US 2013/0029974 A1      Jan. 31, 2013

(30) Foreign Application Priority Data
Jan. 29, 2010    (EP) .................................... 10152132

(51) Int. Cl.
| | | |
|---|---|---|
| A61K 31/55 | (2006.01) | |
| A61K 31/541 | (2006.01) | |
| A61K 31/4985 | (2006.01) | |
| A61K 31/5377 | (2006.01) | |
| A61P 31/00 | (2006.01) | |
| A61P 35/00 | (2006.01) | |
| C07D 487/04 | (2006.01) | |
| C40B 40/04 | (2006.01) | |

(52) U.S. Cl.
USPC .................. 514/217.05; 514/233.2; 514/249; 514/228.5; 544/58.6; 544/350; 544/117; 540/599; 506/15

(58) Field of Classification Search
USPC ...................... 514/217.05, 249, 228.5, 233.2; 540/599; 544/58.6, 117, 350; 506/15
See application file for complete search history.

(56) References Cited

FOREIGN PATENT DOCUMENTS

| EP | 0 152 077 | 8/1985 |
|---|---|---|
| RU | 2 281 947 C1 | 8/2006 |
| WO | WO 2004/026877 A1 | 4/2004 |
| WO | WO 2004/048363 A1 | 6/2004 |
| WO | WO 2009/156951 A2 | 12/2009 |

OTHER PUBLICATIONS

Cohen P., "The Development and Therapeutic Potential of Protein Kinase Inhibitors", *Current Opinion in Chemistry Biology* 3:459-465 (1999).
Velculescu V.E., "Defining the Blueprint of the Cancer Genome", *Carcinogenesis* 29(6):1087-1091 (2008).
Palmer B.D. et al., "Structure-Activity Relationships for 5-Substituted 1-Phenylbenzimidazoles as Selective Inhibitors of the Platelet-Derived Growth Factor Receptor", *J. Med. Chem.* 42:2373-2382 (1999).
Lackey K. et al., "The Discovery of Potent cRaf1 Kinase Inhibitors", *Bioorganic & Medicinal Chemistry Letters* 10:223-226 (2000).
Koresawa M. et al., "High-Throughput Screening With Quantitation of ATP Consumption: A Universal Non-Radioisotope, Homogeneous Assay for Protein Kinase", *ASSAY and Drug Development Technologies* 2(2):153-160 (2004).
International Search Report dated Mar. 2, 2011 issued in PCT/EP2011/050846.

*Primary Examiner* — San-Ming Hui
*Assistant Examiner* — Kathrien Cruz
(74) *Attorney, Agent, or Firm* — Scully, Scott, Murphy & Presser, P.C.

(57) ABSTRACT

There are provided 3,5-disubstituted derivatives of 6,7-dihydroimidazo[1,5-a]pyrazin-8(5H)-one compounds of formula (I) or a pharmaceutically acceptable salt thereof as defined in the present specification, which modulate the activity of protein kinases. The compounds are therefore useful in treating diseases caused by dysregulated protein kinase activity. In particular, such diseases to be treated with a compound of formula (I) of the present invention is one caused by and/or associated with disregulated protein kinase activity selected from the group consisting of cancer, viral infection, prevention of AIDS development in HIV-infected individuals, cell proliferative disorders, autoimmune and neurodegenerative disorders. The present invention also relates to processes for preparing the compounds of formula (I), combinatorial libraries thereof, pharmaceutical compositions comprising them, and methods of treating diseases utilizing pharmaceutical compositions comprising a compound of formula (I).

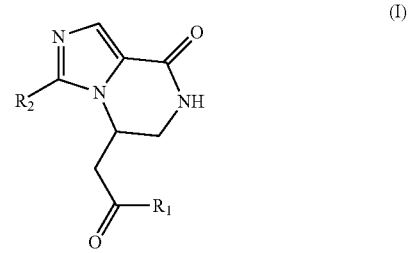

8 Claims, No Drawings

6,7-DIHYDROIMIDAZO[1,5-A]PYRAZIN-8(5H)-ONE DERIVATIVES AS PROTEIN KINASE MODULATORS

The present invention relates to certain 3,5-disubstituted derivatives of 6,7-dihydroimidazo[1,5-a]pyrazin-8(5H)-one compounds, which modulate the activity of protein kinases. The compounds of this invention are therefore useful in treating diseases caused by dysregulated protein kinase activity. The present invention also relates to methods for preparing these compounds, combinatorial libraries thereof, pharmaceutical compositions comprising these compounds, and methods of treating diseases utilizing pharmaceutical compositions comprising these compounds. The malfunctioning of protein kinases (PKs) is the hallmark of numerous diseases. A large share of the oncogenes and proto-oncogenes involved in human cancers code for PKs. The enhanced activities of PKs are also implicated in many non-malignant diseases, such as benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis.

PKs are also implicated in inflammatory conditions and in the multiplication of viruses and parasites. PKs may also play a major role in the pathogenesis and development of neurodegenerative disorders.

For general reference to PKs malfunctioning or disregulation see, for instance, Current Opinion in Chemical Biology 1999, 3, 459-465 and Carcinogenesis 2008, 29, 1087-191.

Fused imidazole derivatives as inhibitors of activated blood coagulation factor X and useful as anticoagulants are disclosed in the patent application WO2004048363 in the name of Takeda Chemical Industries, Ltd., Japan. 7,8-Dihydroimidazo[1,5-a]pyrazin-8-one derivatives having inotropic effect are disclosed in the patent application EP152077 in the name of USV Pharmaceutical Corp., USA.

The present inventors have now discovered that the new compounds of formula (I), described below, are kinase inhibitors and are thus useful in therapy as antitumor agents.

Accordingly, a first object of the present invention is to provide a 6,7-dihydroimidazo[1,5-a]pyrazin-8(5H)-one compound of the formula (I):

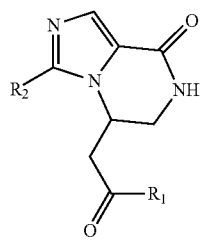

I wherein:
$R_1$ is —$NR_3R_4$ or —$OR_3$;
R2 is a hydrogen atom or an optionally substituted group selected from straight or branched $C_1$-$C_6$ alkyl, aryl, heteroaryl, aryl $C_1$-$C_6$ alkyl and heteroaryl $C_1$-$C_6$ alkyl;
$R_3$ and $R_4$, the same or different, are each independently hydrogen atom or an optionally substituted group selected from straight or branched $C_1$-$C_6$ alkyl, $C_2$-$C_6$ alkenyl, $C_2$-$C_6$ alkynyl, $C_3$-$C_6$ cycloalkyl, cycloalkyl $C_1$-$C_6$ alkyl, heterocyclyl, heterocyclyl $C_1$-$C_6$ alkyl, aryl, aryl $C_1$-$C_6$ alkyl, heteroaryl and heteroaryl $C_1$-$C_6$ alkyl, or $R_3$ and $R_4$, taken together with the nitrogen atom to which they are bonded, may form an optionally substituted 3 to 7 membered heterocyclyl or heteroaryl ring, optionally containing one additional heteroatom or heteroatomic group selected from S, O, N and NH; or a pharmaceutically acceptable salt thereof.

The present invention also provides methods of synthesizing the 3,5-disubstituted-6,7-dihydroimidazo[1,5-a]pyrazin-8(5H)-one compounds, represented by formula (I), prepared through a process consisting of standard synthetic transformations.

The invention provides a compound of formula (I) or a pharmaceutically acceptable salt thereof, as defined above, for use as a medicament. In particular, the present invention provides a compound of formula (I) as above defined for treating diseases caused by and/or associated with disregulated protein kinase activity, particularly ABL, ACK1, AKT1, ALK, AUR1, AUR2, BRK, BUB1, CDC7/DBF$_4$, CDK2/CYCA, CHK1, CK2, EEF2K, EGFR1, EphA2, EphB4, ERK2, FAK, FGFR1, FLT3, GSK3beta, Haspin, IGFR1, IKK2, IR, JAK1, JAK2, JAK3, KIT, LCK, LYN, MAPKAPK2, MELK, MET, MNK2, MPS1, MST4, NEK6, NIM1, P38alpha, PAK-4, PDGFR, PDK1, PERK, PIM1, PIM2, PKAalpha, PKCbeta, PLK1, RET, ROS1, SULU1, Syk, TLK2, TRKA, TYK, VEGFR2, VEGFR3, ZAP70.

A preferred pharmaceutical use of a compound of formula (I) of the present invention is for treating a disease caused by and/or associated with disregulated protein kinase activity selected from the group consisting of cancer, viral infection, prevention of AIDS development in HIV-infected individuals, cell proliferative disorders, autoimmune and neurodegenerative disorders.

Another preferred pharmaceutical use of the compounds of the present invention is for treating specific types of cancer including but not limited to: carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage including leukaemia, acute lymphocytic leukaemia, acute lymphoblastic leukaemia, B-cell lymphoma, T-cell-lymphoma, Hodgkin's lymphoma, non-Hodgkin's lymphoma, hairy cell lymphoma and Burkitt's lymphoma; hematopoietic tumors of myeloid lineage, including acute and chronic myelogenous leukemias, myelodysplastic syndrome and promyelocytic leukaemia; tumors of mesenchymal origin, including fibrosarcoma and rhabdomyosarcoma; tumors of the central and peripheral nervous system, including astrocytoma neuroblastoma, glioma and schwannomas; other tumors, including melanoma, seminoma, teratocarcinoma, osteosarcoma, xeroderma pigmentosum, keratoxanthoma, thyroid follicular cancer and Kaposi's sarcoma.

Another preferred pharmaceutical use of the compounds of the present invention is for treating specific cellular proliferation disorders such as, for example, benign prostate hyperplasia, familial adenomatosis polyposis, neurofibromatosis, psoriasis, vascular smooth cell proliferation associated with atherosclerosis, pulmonary fibrosis, arthritis, glomerulonephritis and post-surgical stenosis and restenosis.

In an analogous way, the present invention also provides a method for treating any of the above noted diseases.

The compounds of this invention may be useful in inhibiting tumour angiogenesis and metastasis, as well as in the treatment of organ transplant rejection and host versus graft disease.

The present invention further provides a method of treatment comprising a compound of formula (I) in combination with radiation therapy or chemotherapy regimen for simultaneous, separate or sequential use in anticancer therapy. Moreover the invention provides an in vitro method for inhibiting protein kinase activity which comprises contacting the said protein kinase with an effective amount of a compound of formula (I).

The present invention also provides a pharmaceutical composition comprising one or more compounds of formula (I) or a pharmaceutically acceptable salt thereof and a pharmaceutically acceptable excipient, carrier or diluent.

The present invention also provides a pharmaceutical composition comprising a compound of formula (I) in combination with known cytostatic or cytotoxic agents, antibiotic-type agents, DNA damaging or intercalating agents, platin-based agents, alkylating agents, antimetabolite agents, hormonal agents, antihormonal agents such as antiestrogens, antiandrogens and aromatase inhibitors, immunological agents, interferon-type agents, cyclooxygenase inhibitors (e.g. COX-2 inhibitors), matrixmetalloprotease inhibitors, tyrosine kinase inhibitors, other kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, inhibitors of kinesins, therapeutic monoclonal antibodies, inhibitors of mTOR, histone deacetylase inhibitors, inhibitors of hypoxic response and the like, for simultaneous, separate or sequential use in anticancer therapy. Additionally, the invention provides a product or kit comprising a compound of formula (I) or a pharmaceutically acceptable salt thereof, as defined above, or pharmaceutical compositions thereof and one or more chemotherapeutic agents, as a combined preparation for simultaneous, separate or sequential use in anticancer therapy.

Moreover the invention provides the use of a compound of formula (I) or a pharmaceutically acceptable salt thereof, as defined above, in the manufacture of a medicament with antitumor activity.

Finally, the invention provides a compound of formula (I) or a pharmaceutically acceptable salt thereof, as defined above, for use in a method of treating cancer.

Unless otherwise specified, when referring to the compounds of formula (I) per se as well as to any pharmaceutical composition thereof or to any therapeutic method of treatment comprising them, the present invention includes all the hydrates, solvates, N-oxides and pharmaceutically acceptable salts of the compounds of this invention.

N-oxides are compounds of formula (I) wherein nitrogen and oxygen are tethered through a dative bond.

All forms of chiral isomers or other forms of isomers including enantiomers and diastereomers, are intended to be covered herein. Compounds containing a chiral center may be used as a racemic mixture or as an enantiomerically enriched mixture, or the racemic mixture may be separated using well-known techniques and an individual enantiomer may be used alone.

In cases wherein compounds may exist in tautomeric forms, such as keto-enol tautomers, each tautomeric form is contemplated as being included within this invention whether existing in equilibrium or predominantly in one form.

In the present description, unless otherwise indicated, with the term "straight or branched $C_1$-$C_6$ alkyl" we intend any group such as, for instance, methyl, ethyl, n-propyl, isopropyl, n-butyl, isobutyl, sec-butyl, tert-butyl, n-pentyl, n-hexyl, and the like.

With the term "straight or branched $C_2$-$C_6$ alkenyl" or "straight or branched $C_2$-$C_6$ alkynyl" we intend any of the unsaturated alkenyl or alkynyl groups with from 2 to 6 carbon atoms for instance including vinyl, allyl, 1-propenyl, isopropenyl, 1-, 2- or 3-butenyl, pentenyl, hexenyl, ethynyl, 1- or 2-propynyl, butynyl, pentynyl, hexynyl, and the like.

With the term "$C_3$-$C_6$ cycloalkyl" we intend, unless otherwise specified, 3- to 6-membered all-carbon monocyclic ring, which may contain one or more double bonds but does not have a completely conjugated π-electron system. Examples of cycloalkyl groups, without limitation, are cyclopropane, cyclobutane, cyclopentane, cyclopentene, cyclohexane, cyclohexene and cyclohexadiene.

With the term "heterocyclyl" we intend a 3- to 7-membered, saturated or partially unsaturated carbocyclic ring where one or more carbon atoms are replaced by heteroatoms such as nitrogen, oxygen and sulfur. Non limiting examples of heterocyclyl groups are, for instance, pyrane, pyrrolidine, pyrroline, imidazoline, imidazolidine, pyrazolidine, pyrazoline, thiazoline, thiazolidine, dihydrofuran, tetrahydrofuran, 1,3-dioxolane, piperidine, piperazine, morpholine and the like.

With the term "aryl" we intend a mono-, bi- or poly-carbocyclic hydrocarbon with from 1 to 4 ring systems, optionally further fused or linked to each other by single bonds, wherein at least one of the carbocyclic rings is "aromatic", wherein the term "aromatic" refers to completely conjugated π-electron bond system. Non-limiting examples of such aryl groups are phenyl, α- or β-naphthyl or biphenyl groups.

With the term "heteroaryl" we intend aromatic heterocyclic rings, typically 5- to 7-membered heterocycles with from 1 to 3 heteroatoms selected among N, O or S; the heteroaryl ring can be optionally further fused or linked to aromatic and non-aromatic carbocyclic and heterocyclic rings. Not limiting examples of such heteroaryl groups are, for instance, pyridyl, pyrazinyl, pyrimidinyl, pyridazinyl, indolyl, imidazolyl, thiazolyl, isothiazolyl, pyrrolyl, phenyl-pyrrolyl, furyl, phenyl-furyl, oxazolyl, isoxazolyl, pyrazolyl, thienyl, benzothienyl, isoindolinyl, benzoimidazolyl, quinolinyl, isoquinolinyl, 1,2,3-triazolyl, 1-phenyl-1,2,3-triazolyl, 2,3-dihydroindolyl, 2,3-dihydrobenzofuranyl, 2,3-dihydrobenzothiophenyl; benzopyranyl, 2,3-dihydrobenzoxazinyl, 2,3-dihydroquinoxalinyl and the like.

According to the meanings provided to $R_2$, $R_3$ and $R_4$, any of the above groups may be further optionally substituted in any of their free positions by one or more groups, for instance 1 to 6 groups, selected from: halogen, nitro, oxo groups (=O), carboxy, cyano, $C_1$-$C_6$ alkyl, polyfluorinated alkyl, $C_2$-$C_6$ alkenyl, $C_2$-$C_6$ alkynyl, $C_3$-$C_6$ cycloalkyl, heterocyclyl, aryl, heteroaryl; amino groups and derivatives thereof such as, for instance, alkylamino, dialkylamino, arylamino, diarylamino, ureido, alkylureido or arylureido; carbonylamino groups and derivatives thereof such as, for instance, formylamino, alkylcarbonylamino, alkenylcarbonylamino, arylcarbonylamino, alkoxycarbonylamino; hydroxy groups and derivatives thereof such as, for instance, alkoxy, polyfluorinated alkoxy, aryloxy, alkylcarbonyloxy, arylcarbonyloxy, cycloalkenyloxy or alkylideneaminoxy; carbonyl groups and derivatives thereof such as, for instance, alkylcarbonyl, arylcarbonyl, alkoxycarbonyl, aryloxycarbonyl, cycloalkyloxycarbonyl, aminocarbonyl, alkylaminocarbonyl, dialkylaminocarbonyl; sulfurated derivatives such as, for instance, alkylthio, arylthio, alkylsulfonyl, arylsulfonyl, alkylsulfinyl, arylsulfinyl, arylsulfonyloxy, aminosulfonyl, alkylaminosulfonyl or dialkylaminosulfonyl.

In their turn, whenever appropriate, each of the above substituents may be further substituted by one or more of the aforementioned groups.

In the present description, unless otherwise specified, with the term "cyano" we intend a —CN residue.

With the term "nitro" we intend a —NO$_2$ group.

With the term "halogen" we intend a fluorine, chlorine, bromine or iodine atom.

With the term "polyfluorinated alkyl or alkoxy" we intend a straight or branched $C_1$-$C_6$ alkyl or alkoxy group as above defined, wherein more than one hydrogen atom is replaced by fluorine atoms such as, for instance, trifluoromethyl, trifluoromethoxy, 2,2,2-trifluoroethyl, 2,2,2-trifluoroethoxy, 1,2-difluoroethyl, 1,1,1,3,3,3-hexafluoropropyl-2-yl, and the like.

From all of the above, it is clear to the skilled man that any group which name has been identified as a composite name such as, for instance, cycloalkylalkyl, arylalkyl, heterocyclylalkyl, alkoxy, alkylthio, aryloxy, arylalkyloxy, alkylcarbonyloxy and the like, has to be intended as conventionally construed from the parts to which it derives. So far, as an example, the terms heterocyclyl-alkyl and cycloalkyl-alkyl stand for a straight or branched alkyl group being further substituted by a heterocyclic or cycloalkyl group, respectively, as above defined.

The term "pharmaceutically acceptable salts" embraces salts commonly used to form alkali metal salts and to form addition salts of free acids or free bases. The nature of the salt is not critical, provided that it is pharmaceutically acceptable. Suitable pharmaceutically acceptable acid addition salts of the compounds of the present invention may be prepared from an inorganic acid or from an organic acid. Examples of such inorganic acids are hydrochloric, hydrobromic, hydroiodic, nitric, carbonic, sulfuric, and phosphoric acid. Appropriate organic acids may be selected from aliphatic, cycloaliphatic, aromatic, araliphatic, heterocyclic, carboxylic and sulfonic classes of organic acids, examples of which are formic, acetic, trifluoroacetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, stearic, cyclohexylaminosulfonic, algenic, hydroxybutyric, galactaric and galacturonic acid. Suitable pharmaceutically acceptable base addition salts of the compounds of the present invention include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methyl-glucamine) and procaine. All of these salts may be prepared by conventional means from the corresponding compounds of the present invention, for instance by reacting them with the appropriate acid or base.

A preferred class of compounds of the present invention are those of formula (I) wherein $R_1$ is —NH$_2$ or NHR$_3$ and $R_3$ is a straight or branched $C_1$-$C_6$ alkyl or $C_2$-$C_6$ alkenyl group or it is an optionally substituted aryl or arylalkyl group. Also preferred are the compounds of formula (I) wherein $R_2$ is hydrogen or an optionally substituted aryl or heteroaryl group.

For a reference to any specific compound of formula (I) of the invention, optionally in the form of pharmaceutically acceptable salts, see the experimental section.

The present invention also provides a process for the preparation of a compound of formula (I) as defined above, characterized in that the process comprises:

a) decarboxylating a compound of formula (II):

b) reacting the resultant compound of formula (III):

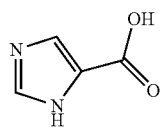

with a compound of formula (IV) or a salt thereof:

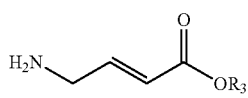

wherein $R_3$ is a $C_1$-$C_6$ alkyl group, so as to obtain a compound of formula (I):

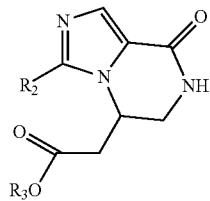

wherein $R_3$ is a $C_1$-$C_6$ alkyl group and $R_2$ is hydrogen, or a pharmaceutically acceptable salt thereof and, if necessary or desired, performing one or more of the following additional steps:

separating the compound of formula (I) into the single isomers;

converting a compound of formula (I) into a different compound of formula (I) by introduction on the imidazole moiety of a $R_2$ group as defined above different from hydrogen;

converting a compound of formula (I) into a different compound of formula (I) by replacing the group —OR$_3$ with a different group $R_1$ as defined above;

converting a compound of formula (I) into a pharmaceutically acceptable salt or converting a salt into the free compound (I).

The present invention also provides a process for the preparation of a compound of formula (III) as defined above, characterized in that the process comprises:

a) decarboxylating a compound of formula (II) as defined above.

The present invention further provides a process for the preparation of a compound of formula (I) as defined above, characterized in that the process comprises:

b) reacting a compound of formula (III) as defined above with compound of formula (IV) or a salt thereof as defined above so as to obtain a compound of formula (I):

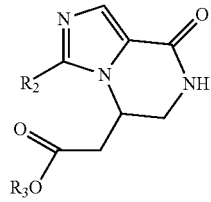

wherein $R_3$ is a $C_1$-$C_6$ alkyl group and $R_2$ is hydrogen, or a pharmaceutically acceptable salt thereof and, if necessary or desired, performing one or more of the following additional steps:

separating the compound of formula (I) into the single isomers;

converting a compound of formula (I) into a different compound of formula (I) by introduction on the imidazole moiety of a $R_2$ group as defined above different from hydrogen;

converting a compound of formula (I) into a different compound of formula (I) by replacing the group —$OR_3$ with a different group $R_1$ as defined above;

converting a compound of formula (I) into a pharmaceutically acceptable salt or converting a salt into the free compound (I).

Conversions of a compound of formula (I) into another compound of formula (I) can be carried out for example with one or more of the following reactions:

c) reaction of a compound of formula (I) wherein $R_3$ is $C_1$-$C_6$ alkyl, and $R_2$ is hydrogen with a compound of formula $R_2$—Z (V), wherein $R_2$ is as above defined but not hydrogen and Z is a halogen, so as to obtain a compound of formula (I):

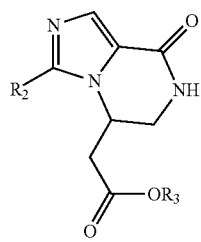

wherein $R_3$ is $C_1$-$C_6$ alkyl and $R_2$ is as above defined but not hydrogen;

d.1) acid or basic hydrolysis of a compound of formula (I) wherein $R_3$ is $C_1$-$C_6$ alkyl so as to obtain a compound of formula (I) wherein $R_1$ is —OH, or a salt thereof;

d.2) transesterification of a compound of formula (I) wherein $R_3$ is a $C_1$-$C_6$ alkyl, by reactions with a compound of formula $R_3$—OH (VI) wherein $R_3$ is a different $C_1$-$C_6$ alkyl so as to obtain a compound of formula (I) wherein $R_3$ is a different $C_1$-$C_6$ alkyl;

d.3) aminolysis of a compound of formula (I) wherein $R_3$ is $C_1$-$C_6$ alkyl, by reaction with a compound of formula H—$NR_3R_4$ (VII) wherein $R_3$ and $R_4$ are as defined above so as to obtain a compound of formula (I) wherein $R_1$ is —$NR_3R_4$ and $R_3$ and $R_4$ are as defined above;

d.4) esterification of a compound of formula (I) wherein $R_1$ is —OH or a salt thereof by reactions with a compound of formula (VI) as defined above, so as to obtain a compound of formula (I) wherein $R_1$ is —$OR_3$ and $R_3$ is as defined above but not hydrogen;

d.5) amidation of a compound of formula (I) wherein $R_1$ is —OH or a salt thereof by reaction with a compound of formula (VII) as defined above so as to obtain a compound of formula (I) wherein $R_1$ is —$NR_3R_4$ and $R_3$ and $R_4$ are as defined above.

Likewise, the conversion of a compound of formula (I) into a pharmaceutically acceptable salt thereof or, alternatively, the conversion into the free compound (I) of a corresponding salt, according to procedures well-known in the art, is still within the scope of the invention.

When preparing the compounds of formula (I) according to any variant of the process, which are all to be intended as within the scope of the invention, optional functional groups within the starting materials, the reagents or the intermediates thereof, and which could give rise to unwanted side reactions, need to be properly protected according to conventional techniques.

The present invention further provides processes for the preparation of a compound of formula (I) as defined above, characterized in that the process comprises:

b') reacting a compound of formula (III'):

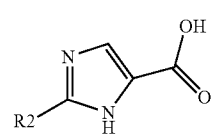

wherein $R_2$ is as defined above but not hydrogen or a suitable precursor group thereof, with a compound of formula (IV) or a salt thereof as defined above so as to obtain a compound of formula (I):

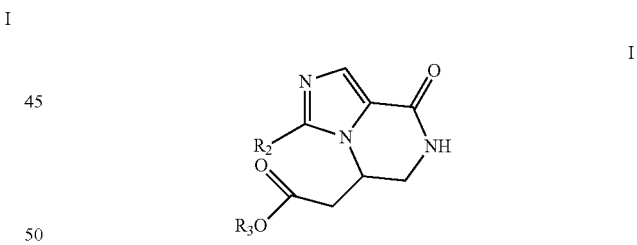

wherein $R_3$ is a $C_1$-$C_6$ alkyl group and $R_2$ is as defined above but not hydrogen, or a pharmaceutically acceptable salt thereof and, if necessary or desired, performing one or more of the necessary additional steps described above, including the conversion of a precursor moiety of a $R_2$ group as defined above different from hydrogen into the desired $R_2$ group by means of suitable chemical reactions.

The starting materials of the process object of the present invention, comprehensive of any possible variant, as well as any reactant thereof, are known compounds and if not commercially available per se may be prepared according to well-known methods.

For example, compounds of formula (II), (III) and (III') are commercially available or can be prepared according to known methods.

The compounds of formula (IV) are prepared starting from the corresponding 4-bromocrotonates that in their turn are commercially available or can be prepared according to well-known methods.

For example the 4-amino ethylcrotonate can be prepared through the following steps:
e) reacting ethyl-4-bromo ethylcrotonate of formula (VIII):

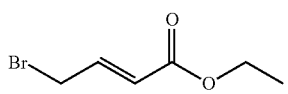

VIII with commercially available diformylimide sodium salt of formula (IX):

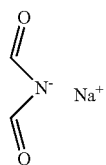

IX f) hydrolysing in acidic conditions the resultant compound of formula (X):

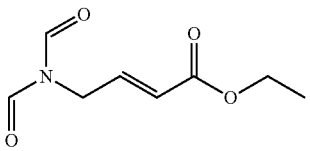

X so as to obtain a compound of formula (IV) wherein $R_3$ is ethyl.

The compounds of formula (V), (VI) and (VII) are known or easily obtained according to known methods, for a general reference see: Smith, Michael—March's Advanced Organic Chemistry: reactions mechanisms and structure—$5^{th}$ Edition, Michael B. Smith and Jerry March, John Wiley & Sons Inc., New York (NY), 2001.

According to step (a) of the process, decarboxylation of the compound of formula (II) can be carried out in a variety of ways according to different methods. Preferably, it is carried out in an appropriate solvent such as 1-methyl-pyrrolidin-2-one or dimethylacetamide (DMA), at a temperature between 100° and 170° C. for a period from 4 to 48 h under conventional heating or microwaves irradiation.

According to step (b) and (b') of the process, the conversion of the compound of formula (III) or (III') into a compound of formula (I) as above defined can be carried out in a variety of ways according to different methods. Such methods are useful for obtaining amido derivatives from the corresponding carboxylic acid and for cyclising the resultant intermediate into the desired compound of formula (I) as defined above, for example in the presence of a base. Preferably, the carboxylic acid of formula (III) or (III') is firstly activated to the acid chloride, by reaction with thionyl or oxalyl chloride, and then reacted with an ammonium salt of, preferably trifluoroacetate salt of a compound of formula (IV), and at the same time cyclised in presence of pyridine under reflux for a time ranging from 6 to 8 hours.

According to conversion step (c), the preparation of a derivative of formula (I) wherein $R_2$ is as defined above but not hydrogen, starting from the compound of formula (I) where $R_2$ is hydrogen can be carried out in a variety of ways, according to conventional methods. Preferably the reaction of step (c) is carried out through a C—H activation coupling between the compound of formula (V) as defined above with a compound of formula (I) where $R_2$ is H, so as to obtain a compound of formula (I) where $R_2$ is a group as defined above but not hydrogen atom, in the presence of a Pd-catalyst and an additive such as copper (I) iodide, using N,N-dimethylformamide or N,N-dimethylacetamide as solvent, at a temperature of from 120° to 165° C. for a time between 3 and 5 hours if the reaction was performed under microwaves irradiation, or 18-36 hours under conventional heating.

According to any one of steps (d.1-d.5) the conversion of a compound of formula (I) in another compound of formula (I), can be carried out in a variety of ways, according to different methods.

Preferably according to step (d.1) of the process, the hydrolysis of a compound of formula (I) wherein $R_1$ is —OCH$_2$CH$_3$, so as to obtain a compound of formula (I) wherein $R_1$ is —OH can be carried out under acidic or basic conditions. Preferably, the reaction is carried out under basic conditions. According to the operative conditions being employed, the compound of formula (I) wherein $R_1$ is —OH can be obtained either in its acidic form or, alternatively, as a salt.

Preferably according to step (d.2) of the process, the transesterification of a compound of formula (I) wherein $R_1$ is —OCH$_2$CH$_3$, so as to obtain a compound of formula (I) wherein $R_3$ is an alkyl different from ethyl, can be carried out by reaction with a compound of formula (VII) as defined above in an appropriate solvent, such as the compound of formula (VII) as defined above itself or dioxane at the refluxing temperature, optionally in the presence of a suitable metal based catalysts, like dibutylin oxide or titanium alkoxides such as, for instance, titanium (IV) ethoxide, titanium (IV) isopropoxide and the like.

Preferably according to step (d.3) of the process, the aminolysis of a compound of formula (I) wherein $R_1$ is —OCH$_2$CH$_3$, so as to obtain a compound of formula (I) wherein $R_1$ is —NR$_3$R$_4$, can be carried out in an appropriate solvent such as dioxane or dichloromethane, optionally in the presence of a suitable metal based catalysts, like trimethyl aluminium or DABAL.

Preferably according to step (d.4) of the process, the esterification of a compound of formula (I) wherein $R_1$ is a group —OH so as to obtain a compound of formula (I) wherein $R_1$ is —OR$_3$, can be carried out in the presence of a suitable condensing agent, for instance dicyclohexylcarbodiimide (DCC), 1-ethyl-3-(3'-dimethylaminopropyl)carbodiimide (EDC), 3,4-dihydro-3-hydroxy-4-oxo-1,2,3-benzotriazine (DHBTOH), O-benzotriazolyltetramethylisouronium tetrafluoroborate (TBTU), or benzotriazol-1-yloxytripyrrolidinophosphonium hexafluorophosphate (PyBOP), in an appropriate solvent such as dichloromethane, dimethylformamide.

Preferably according to step (d.5) of the process, the amidation of a compound of formula (I) wherein $R_1$ is —OH so as to obtain a compound of formula (I) wherein $R_1$ is —NR$_3$R$_4$ can be carried out in a variety of ways, according to conventional methods for obtaining amido derivatives from the corresponding acids. Preferably, the reaction is carried out by reaction with compound of formula (VII) as defined above after activation of the carboxylic function of the compound of formula (I) by reaction with thionyl or oxalyl chloride, TFFH or alternatively in the presence of a suitable condensing agent, for instance dicyclohexylcarbodiimide (DCC), 1-ethyl-3-(3'-dimethylaminopropyl)carbodiimide (EDC), 3,4-dihydro-3-hydroxy-4-oxo-1,2,3-benzotriazine (HBTOH), O-benzotriazolyltetramethylisouronium tetrafluoroborate (TBTU) or benzotriazol-1-yloxytripyrrolidinophosphonium hexafluorophosphate (PyBOP), in an appropriate solvent such as dichloromethane, and/or dimethylformamide.

In addition to the above, the compounds of formula (I) may be advantageously prepared according to combinatorial chemistry techniques widely known in the art, by accomplishing the aforementioned reactions between the intermediates in a serial manner and by working under solid-phase-synthesis (SPS) conditions wherein the resin is a commercially available polystyrenic resin including, for instance, Wang resin, Trityl resin, Cl-trityl resin, Rink amide resin, Tentagel OH resin and derivatives thereof.

Clearly, by working according to combinatorial chemistry techniques as formerly indicated, a plurality of compounds of formula (I) may be obtained.

Hence, it is a further object of the present invention a library of two or more compounds of formula (I)

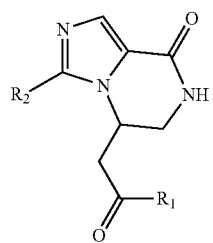

wherein $R_1$ and $R_2$ are as defined above.

According to a preferred embodiment of the invention, the aforementioned library comprises the compounds of formula (I) wherein $R_1$ is —$NH_2$ or $NHR_3$, and $R_3$ is a straight or branched $C_1$-$C_6$ alkyl or $C_2$-$C_6$ alkenyl group or it is an optionally substituted aryl or arylalkyl group.

Also preferred is a library of compounds of formula (I) wherein $R_2$ is hydrogen or an optionally substituted aryl or heteroaryl group.

For a general reference to the above libraries of compounds of formula (I) see the experimental section.

From all of the above, it is clear to the skilled person that once a library of 6,7-dihydroimidazo[1,5-a]pyrazin-8(5H)-one derivatives is thus prepared, for instance consisting of thirty eight compounds of formula (I), the said library can be very advantageously used for screening towards given kinases, as formerly reported.

See, for a general reference to libraries of compounds and uses thereof as tools for screening biological activities, J. Med. Chem. 1999, 42, 2373-2382; and Bioorg. Med. Chem. Lett. 10 (2000), 223-226.

Pharmacology

The inhibiting activity of putative kinase inhibitors and the potency of selected compounds is determined through a method of assay based on the use of the Kinase-Glo® Luminescent Kinase Assay (commercially available from Promega corporation and described in Koresawa, M. and Okabe, T. (2004) High-throughput screening with quantitation of ATP consumption: A universal non-radioisotope, homogeneous assay for protein kinase. *Assay Drug Dev. Technol.* 2, 153-60).

The depletion of ATP as a result of kinase activity can be monitored in a highly sensitive manner through the use of Kinase-Glo® or Kinase-Glo® Plus Reagent, which uses luciferin, oxygen and ATP as substrates in a reaction that produces oxyluciferin and light.

The short forms and abbreviations used herein have the following meaning:
ATP Adenosine triphosphate
BSA bovine serum albumine
Tris 2-Amino-2-(hydroxymethyl)-1,3-propanediol
Hepes N-(2-Hydroxyethyl)piperazine-N'-(2-ethanesulfonic acid)
DTT threo-1,4-Dimercapto-2,3-butanediol
TFFH tetramethylfluoroformamidinium hexafluorophosphate
THF tetrahydrofuran
MTBE methyl tertiary butyl ether
DIPEA diisopropylethylamine
PyBOP benzotriazol-1-yloxytris(pyrrolidino)phosphonium exafluorophosphate
DABAL adduct of trimethylaluminum and 1,4-diazabicyclo[2.2.2]octane
EDC 1-ethyl-3-(3'-dimethylaminopropyl)carbodiimide
DHBTOH 3,4-dihydro-3-hydroxy-4-oxo-1,2,3-benzotriazine
TFA trifluoroacetic acid
TMOF trimethyl orto formate
DCE dichloroethane
DCM dichloromethane
DMF dimethylformamide
DMA dimethylacetamide
DMSO dimethylsulfoxide
KDa kiloDalton
mg milligram
μg microgram
ng nanogram
L liter
mL milliliter
μL microliter
M molar
mM millimolar
μM micromolar
nM nanomolar
r.t. retention time Kinase reaction conditions are target (enzyme) dependent and thus undergo individual adaptations. The Kinase-Glo® Luminescent Kinase Assay can be used with virtually any kinase and substrate combination.

Also the buffer conditions may vary depending on the kinase of interest (e.g for PKA a composition of 40 mM Tris pH 7.5, 20 mM $MgCl_2$, 0.1 mg/ml BSA, in 50 μl final volume is used). Typically the range of ATP titration is 0.1 μM to 10 μM.

The optimal kinase substrate results in the greatest change in luminescence when comparing kinase reaction wells with no kinase wells.

The optimal amount of kinase is determined by making two fold serial dilutions across plates using the optimal amount of ATP and optimal kinase substrate. The optimal amount of kinase to use in subsequent compound screens and IC50 determinations is the amount required for luminescence to be within the linear range of the kinase titration curve (sigmoidal dose response).

Robotized Kinase-Glo® Assay

This assay was set up for the measurement of kinase activity and/or inhibition. It is homogeneous, suitable for all type of protein kinases, quick and radioactivity-free.

We established the assay in 384 well-plates: the test mix consisted of:
1) 3× Enzyme mix (done in Kinase Buffer 3×), 5 μl/well
2) 3× substrate and ATP mix (done in D₂0), 5 μl/well
3) 3× compound of formula (I) (diluted into D₂0—3% DMSO)—5 μl/well)

As an outcome, the percentage of inhibition at 10 μM was evaluated for each compound tested: see below for compound dilution and assay scheme. Each enzyme had its own buffer constitution, substrate type and concentration. Incubation time instead was 90 min for all targets.

Test compounds were received as a 1 mM solution in 100% DMSO into 96 well plates. The plates were diluted to 30 μM in D₂O, 3% DMSO; 4 plates are reorganized in 384 well plate by dispensing 5 μl of each 96 wp into the four quadrants of a 384 wp. In well P23 and P24 the internal standard inhibitor staurosporine was added.

Assay Scheme

Test plates were first added with 5 μl of the compound dilution (30 μM, corresponding to 3× dilution) and then loaded onto a robotized station together with one reservoir for the Enzyme mix (3×) and one for the ATP mix (3×), specific for each target under study.

To start the assay, the robot aspirated 5 μl of ATP/Substrate mix, made an air gap inside the tips (5 μl) and aspirated 5 μl of Enzyme mix. The subsequent dispensation into the test plates allowed the kinase reaction to start after 3 cycles of mixing, done by the robot itself by up and down pipetting. At this point, the correct concentration was restored for all reagents.

The robot incubated the plates for 90 minutes at room temperature, and then stopped the reaction by pipetting 15 μl of Kinase-Glo® reagent into the reaction mix. Three cycles of mixing were done immediately after the addition of the reagent.

The principle of the Kinase-Glo® technique is the presence in the reagent mixture of oxygen, luciferin and luciferase enzyme: in the presence of ATP, remaining from the kinase reaction, oxi-luciferin is produced with the emission of light, directly dependent on the amount of ATP. For optimal performances of this technique, the kinase reaction should utilize at least 15-20% of the available ATP.

After another 60 minutes of incubation to stabilize the luminescent signal, the plates were read on a ViewLux® instrument. Data were analyzed using the software package Assay Explorer® that provided percent inhibition data.

As example herein are reported the assay conditions used for testing the compounds of formula (I) against ALKtide YFF APCo kinase;

ATP concentration: 1 μM
Enzyme concentration: 100 nM
Reaction buffer: Hepes 50 mM pH 7.5, MgCl₂ 5 mM, MnCl₂ 1 mM, DTT 1 mM, Na₃VO₄ uM, 0.2 mg/ml BSA Assay procedure: add 5 ul compound of formula (I) (3×), add 5 μl ATP/S mix (3×) in buffer 1×; add 5 μl enzyme in buffer 2×+3×BSA; for the blank, add 5 μl buffer 2×+3×BSA without enzyme. After 90 minutes of incubation, add 15 μl/well of Kinase-Glo reagent. After 60-90 minutes of incubation to stabilize the luminescent signal, the plates are read on a ViuwLux instrument.

The inhibitory activity of putative kinase inhibitors and the potency of selected compounds were also determined using a trans-phosphorylation assay.

Specific peptide or protein substrates are trans-phosphorylated by their specific ser-thr or tyr kinase in the presence of ATP traced with ³³P-γ-ATP, and in the presence of their own optimal buffer and cofactors. At the end of the phosphorylation reaction, more than 98% unlabeled ATP and radioactive ATP is captured by an excess of the ion exchange dowex resin; the resin then settles down to the bottom of the reaction plate by gravity. Supernatant is subsequently withdrawn and transferred into a counting plate, then evaluated by β-counting.

Reaction conditions are target (enzyme) dependent and thus undergo individual adaptations. Also the buffer conditions may vary depending on the kinase of interest. The assay can be used with virtually any kinase and substrate combination and is suitable for all type of protein kinases, such as ABL, ACK1, AKT1, ALK, AUR1, AUR2, BRK, BUB1, CDC7/DBF4, CDK2/CYCA, CHK1, CK2, EEF2K, EGFR1, EphA2, EphB4, ERK2, FAK, FGFR1, FLT3, GSK3beta, Haspin, IGFR1, IKK2, IR, JAK1, JAK2, JAK3, KIT, LCK, LYN, MAPKAPK2, MELK, MET, MNK2, MPS1, MST4, NEK6, NIM1, P38alpha, PAK-4, PDGFR, PDK1, PERK, PIM1, PIM2, PKAalpha, PKCbeta, PLK1, RET, ROS1, SULU1, Syk, TLK2, TRKA, TYK, VEGFR2, VEGFR3, ZAP70.

As example herein are reported the assay conditions used for testing the compounds of formula (I) against MPS1 and CDK2/CYCA.

Inhibition Assay of MPS1 Activity i. Dowex Resin Preparation 500 g of wet resin (SIGMA, custom prepared resin DOWEX 1×8 200-400 mesh, 2.5 Kg) are weighed out and diluted to 2 l in 150 mM sodium formate, pH 3.00.

The resin is allowed to settle down (some hours) and then the supernatant is discarded.

After three washes as above over a couple of days, the resin is allowed to settle and two volumes (wrt the resin volume) of 150 mM sodium formate buffer are added. The pH is then measured and should be around 3.00

The washed resin is stable for more than one week; the stock resin is kept at 4° C. before use.

ii. Kinase Buffer (KB)

The buffer for MPS1 assay was composed of HEPES 50 mM, at pH 7.5, with 2.5 mM MgCl₂, 1 mM MnCl₂, 1 mM DTT, 3 microM Na₃VO₄, 2 mM β-glycerophosphate and 0.2 mg/mL BSA.

iii. Assay Conditions

The assay was run with a final concentration MPS1 of 5 nM, in the presence of 15 microM ATP and 1.5 nM ³³P-γ-ATP; the substrate was P38-β-tide, used at 200 microM.

Inhibition Assay of Cdk2/Cyclin A activity

Kinase reaction: 1.5 μM histone H1 substrate, 25 μATP (0.2 μCi P33γ-ATP), 30 ng of baculovirus co-expressed Cdk2/Cyclin A, 10 μM inhibitor in a final volume of 100 μl buffer (TRIS HCl 10 mM pH 7.5, MgCl₂ 10 mM, 7.5 mM DTT) were added to each well of a 96 U bottom well plate. After 10 min at 37° C. incubation, reaction was stopped by 20 I EDTA 120 mM.

Capture: 100 μl were transferred from each well to Multi-Screen plate, to allow substrate binding to phosphocellulose filter. Plates were then washed 3 times with 150 μl/well PBS Ca⁺⁺/Mg⁺⁺ free and filtered by MultiScreen filtration system.

Detection: filters were allowed to dry at 37° C., then 100 μl/well scintillant were added and 33P labeled histone H1 was detected by radioactivity counting in the Top-Count instrument.

Results: Data are analysed by an internally customized version of the SW package "Assay Explorer" that provides either % inhibition for primary assays or sigmoidal fittings of the ten-dilutions curves for IC₅₀ determination in the secondary assays/hit confirmation routines.

As an example, in Table A below are reported % inhibition data of some compounds of the present invention tested against different kinases.

TABLE A

| Entry | Code | % Inhibition (at 10 microM) | Enzyme |
|---|---|---|---|
| 6 | A3-M-B2 | 80.1 | TRKA |
| 7 | A4-M-B1 | 59.6 | GSK3beta |
| 10 | A7-M-B1 | 66.9 | MPS1 |
| 14 | A9-M-B1 | 53.3 | CDK2/CYCA |
| 12 | A10-M-B1 | 60.6 | GSK3beta |

The compounds of the present invention can be administered either as single agents or, alternatively, in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

If formulated as a fixed dose, such combination products employ the compounds of this invention within the dosage range described below and the other pharmaceutically active agent within the approved dosage range.

Compounds of formula (I) may be used sequentially with known anticancer agents when a combination formulation is inappropriate.

The compounds of formula (I) of the present invention, suitable for administration to a mammal, e.g., to humans, can be administered by the usual routes and the dosage level depends upon the age, weight, conditions of the patient and administration route.

For example, a suitable dosage adopted for oral administration of a compound of formula (I) may range from about 10 to about 500 mg per dose, from 1 to 5 times daily. The compounds of the invention can be administered in a variety of dosage forms, e.g., orally, in the form tablets, capsules, sugar or film coated tablets, liquid solutions or suspensions; rectally in the form suppositories; parenterally, e.g., intramuscularly, or through intravenous and/or intrathecal and/or intraspinal injection or infusion.

The present invention also includes pharmaceutical compositions comprising a compound of formula (I) or a pharmaceutically acceptable salt thereof in association with a pharmaceutically acceptable excipient, which may be a carrier or a diluent.

The pharmaceutical compositions containing the compounds of the invention are usually prepared following conventional methods and are administered in a suitable pharmaceutical form. For example, the solid oral forms may contain, together with the active compound, diluents, e.g., lactose, dextrose saccharose, sucrose, cellulose, corn starch or potato starch; lubricants, e.g., silica, talc, stearic acid, magnesium or calcium stearate, and/or polyethylene glycols; binding agents, e.g., starches, arabic gum, gelatine methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g., syrups, emulsions and suspensions. As an example, the syrups may contain, as carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g., sterile water, olive oil, ethyl oleate, glycols, e.g., propylene glycol and, if desired, a suitable amount of lidocaine hydrochloride.

The solutions for intravenous injections or infusions may contain, as a carrier, sterile water or preferably they may be in the form of sterile, aqueous, isotonic, saline solutions or they may contain propylene glycol as a carrier.

The suppositories may contain, together with the active compound, a pharmaceutically acceptable carrier, e.g., cocoa butter, polyethylene glycol, a polyoxyethylene sorbitan fatty acid ester surfactant or lecithin.

With the aim of better illustrating the present invention, without posing any limitation to it, the following examples are now given.

EXPERIMENTAL SECTION

General Methods

Flash Chromatography was performed on silica gel (Merck grade 9395, 60A). The high-pressure liquid chromatography retention times (HPLC: r.t. values) were determined by:
HPLC Method 1:

A Waters Alliance LC mod. 2795 equipped with a variable UV detector mod 2487, a Chemiluminescence Nitrogen detector (CLND, Antek 8060) and a Waters ZQ2000 mass detector (ESI interface) was used in this application. The total flow was splitted and distributed to the three detectors at a fixed ratio (64:15:21 UV:MS:CLND). The liquid chromatograph was equipped with a 30×3.0 mm I.D. column (Waters xBridge C18, 3.5 um particles), thermostated at 50° C. Two mobile phases were used: phase A was 0.05% w/v formic acid (1 mL/L of 50% formic acid Fluka 09676 in highly purified water) and phase B was 70/25/5 (v/v/v) MeOH/iPrOH/H2O containing 0.035% w/v of formic acid (700 uL/L of 50% formic acid Fluka 09676).

A 5 uL volume of 1 mM nominal sample solution in DMSO was injected (sequential, partial loop mode with no air gaps) and a generic reversed phase gradient analysis (classified as method "IN63SEQ79") was carried out at 0.8 mL/min from 0% to 100% of phase B (v/v) over 5 min, held 0.7 min at 100% B and steeply reverted to 0% B at 5.71 min, with the run stop time set at 6.3 min. The total analysis time ("between injections") was 7.9 min.

The UV detector was operated at 220 nm, 5 Hz sampling rate. The MS device was operated at 3.2 kV capillary voltage, 30 V cone, 2 V extractor, 0.5 V RF lens, 400 L/hr desolvation flow, 100 L/hr cone flow, 100° C. source temperature, 150° C. desolvation temperature, ESI(+) full scan 120-1200 amu acquisition, at 1.7 Hz sampling rate. The CLND detector was operated at 1050° C. furnace temp, 280 mL/min inlet oxygen flow, 80 mL/min inlet argon, 25 mL/min make-up argon, 30 mL/min ozone, 28 torr vacuum, 750 V PMT voltage, PMT chamber at +10° C., sensitivity high, select 5, 4 Hz sampling rate.

HPLC Method 2:

HPLC-MS analyses were performed on a Finnigan MAT mod. LCQ ion trap mass spectrometer, equipped with an ESI (Electrospray) ion source, the mass spectrometer is directly connected to a HPLC SSP4000 (Thermo Separation) equipped with an autosampler Lc Pal (CTC Analytics) and an UV6000LP PDA detector.

HPLC Conditions:
Column: Phenomenex Gemini C18, 3 μm, 50×4.6 mm (default)
Temperature 40° C.
Mobile phase A: Acetate Buffer 5 mM pH 4.5: acetonitrile 95:5 (v:v)
Mobile phase B: Acetate Buffer 5 mM pH 4.5: acetonitrile 5:95 (v:v)
Elution gradient:

| Time (min) | % Mobile Phase A |
|---|---|
| 0 | 100 |
| 7 | 0 |
| 9 | 0 |
| 11 | 100 |
| 13 | 100 |

Flow rate: 1 mL/min
Injection volume: 10 μL
Column temperature: 40° C.

MS Conditions:

The LCQ mass spectrometer operates with an electrospray ionization (ESI) interface in positive and negative ion mode following the operation parameters reported in table 1. MS/MS experiments are performed on the most intense ion of each scan automatically by Xcalibur software. A 45% collision energy was used for the fragmentation of the precursor ions.

TABLE 1

Mass Spectrometer Instrument parameters

| Parameter | Value |
|---|---|
| Capillary Temperature (° C.) | 255 |
| Source Voltage (kV) | 4.00 |
| Capillary Voltage (V) | 21.0 |
| Tube Lens Offset (V) | −5.0 |
| Multipole RF Amplifier (Vp-p) | 400.0 |
| Multipole 1 Offset (V) | −3.00 |
| Multipole 2 Offset (V) | −6.50 |
| InterMultipole Lens Voltage (V) | −16.00 |
| Trap DC Offset Voltage (V) | −10.00 |
| Full Micro scans | 3 |
| Full AGC Target Ions | $5 \times 10^7$ |
| Full Max Ion Time (ms) | 150 |
| MSn Micro scans | 3 |
| MSn AGC Target Ions | $2 \times 10^7$ |
| MSn Max Ion Time (ms) | 200 |
| Electron Multiplier (V) | −950.0 |

HPLC Method 3:

HPLC-MS analyses were performed on a Finnigan MAT mod. LCQ ion trap mass spectrometer, equipped with an ESI (Electrospray) ion source, the mass spectrometer is directly connected to a HPLC SSP4000 (Thermo Separation) equipped with an autosampler Lc Pal (CTC Analytics) and an UV6000LP PDA detector.

HPLC Conditions:
Column: Phenomenex Gemini C18, 3 μm, 50×4.6 mm (default)
Temperature 40° C.
Mobile phase A: Acetate Buffer 5 mM pH 4.5: acetonitrile 95:5 (v:v)
Mobile phase B: Acetate Buffer 5 mM pH 4.5: acetonitrile 5:95 (v:v)
Elution gradient:

| Time (min) | % Mobile Phase A |
|---|---|
| 0 | 100 |
| 2 | 80 |
| 9 | 60 |
| 10 | 0 |
| 12 | 0 |
| 12.10 | 100 |

Flow rate: 1 mL/min
Injection volume: 10 μL
Column temperature: 40° C.

MS Conditions:

The LCQ mass spectrometer operates with an electrospray ionization (ESI) interface in positive and negative ion mode following the operation parameters reported in table 1. MS/MS experiments are performed on the most intense ion of each scan automatically by Xcalibur software. A 45% collision energy was used for the fragmentation of the precursor ions.

Retention times (HPLC r.t.) are given in minutes at 220 nm or at 254 nm. Mass is given as m/z ratio.

HPLC Method 4:

HPLC-MS analyses were performed on Waters 2795 HPLC system equipped with a 996 Waters PDA detector and Micromass mod. ZQ single quadrupole mass spectrometer, equipped with an electrospray (ESI) ion source. Chromatographic condition: Waters Atlantis dC18, 3 μm, 4.6×50 mm column; mobile phase A was ammonium acetate 5 mM buffer (pH 5.2 with acetic acid)/acetonitrile (95:5), and Mobile phase B was H2O/acetonitrile (5:95). Gradient range from 50 to 90% B in 8 minutes. UV detection was performed at 220 nm and 254 nm, flow rate 1 ml/min and 20 μl of injection volume. Full scan, mass range from 100 to 800 amu. Capillary voltage was 3.59 KV; source temp. was 120° C.; cone was 14 V. Retention times (HPLC r.t.) are recorded in minutes at 220 nm or at 254 nm. Mass are given as m/z ratio.

LC Conditions:

| | |
|---|---|
| Column | Waters Atlantis dC18, 3 μm, 4.6 × 50 mm |
| Mobile Phase A | Ammonium acetate 5 mM pH 5.2/Acenotrile 95/5 |
| Mobile Phase B | Acetonitrile/H2O 95/5 |
| Flow Rate | 1 mL/min |

| | Time (min) | % Phase A | % Phase B |
|---|---|---|---|
| Gradient | 0 | 50% | 50% |
| | 8 | 0% | 100% |
| | 10 | 0% | 100% |

| | |
|---|---|
| Injection Volume | 10 μL |
| Column Temperature | 30° C. |
| PDA Channels | 220 nm, 254 nm |

Mass Conditions:

| | |
|---|---|
| Ionization Mode | ESI+ and ESI− |
| Capillary Voltage | 3.48 kV (ES+); 2.76 kV (ES−) |

| | |
|---|---|
| Cone Voltage | 15 V (ES+); 27 V (ES−) |
| Extractor Voltage | 1 V |
| RF Lens Voltage | 0.1 V |
| Source Temperature | 120° C. |
| Desolvation Temperature | 240° C. |
| Cone Gas Flow | 100 L/Hr |
| Desolvation Gas Flow | 600 L/Hr |
| LM Resolution | 15 |
| HM Resolution | 15 |
| Ion Energy | 0.5 |
| Multipler | 600 |
| Scan Mode | Full Scan (Range = 100-800 m/z) ScanTime = 0.5 s Inter-Scan Delay = 0.3 s |

HPLC Method 5:

HPLC-MS analyses were performed on Waters Acquity UPLC™ System was equipped with a Waters Acquity UPLC™ 2996 PDA detector, Waters Acquity ELSD™ detector and Waters Acquity SQ™ (single quadrupole) mass spectrometer, equipped with an electrospray (ESI) ion source.

Chromatographic condition: Waters Acquity UPLC™ BEH C18, 1.7 µm, 2.1×50 mm column; Mobile phase A was 0.05% NH4OH in H2O pH10/Acetonitrile 95/5 and Mobile phase B was H$_2$O/acetonitrile (5:95). Gradient ranged from 50 to 100% B in 2 minutes. UV detected at 220 nm and 254 nm. Flow rate 1 ml/min. Injection volume 20 µl. Full scan, mass range from 100 to 800 amu. Capillary voltage was 3.59 KV; source temp. was 120° C.; cone was 14 V. Retention times (HPLC r.t.) are recorded in minutes at 220 nm or at 254 nm. Mass are given as m/z ratio.

LC Conditions:

| Column | Waters Acquity UPLC ™ BEH C18, 1.7 µm, 2.1 × 50 mm | | |
|---|---|---|---|
| Mobile Phase A | 0.05% NH4OH in H20 pH 10/Acetonitrile 95/5 | | |
| Mobile Phase B | Acetonitrile/H2O 95/5 | | |
| Flow Rate | 0.7 mL/min | | |
| | Time (min) | % Phase A | % Phase B |
| Gradient | 0 | 50% | 50% |
| | 2.1 | 0% | 100% |
| Injection Volume | 1 µL | | |
| Column Temperature | 45° C. | | |
| PDA Channels | 210-350 nm Sampling Rate 10 Resolution 1.2 | | |
| ELSD | Drift Tube 45° C. Nebuliz 12° C. Gain 750 Gas 40 psi | | |

Mass Conditions:

| | |
|---|---|
| Ionization Mode | ESI+ and ESI− |
| Capillary Voltage | 3 kV (ES+); 3 kV (ES−) |
| Cone Voltage | 30 V (ES+); 30 V (ES−) |
| Extractor Voltage | 1 V |
| RF Lens Voltage | 0.1 V |
| Source Temperature | 120° C. |
| Desolvation Temperature | 350° C. |
| Cone Gas Flow | 100 L/Hr |
| Desolvation Gas Flow | 600 L/Hr |
| LM Resolution | 15 |
| HM Resolution | 15 |
| Ion Energy | 0.3 |
| Gain | 1 |
| Scan Mode | Full Scan (Range = 100-800 m/z) ScanTime = 0.1 s Inter-Scan Delay = 0.02 s |

When necessary, the compounds were purified by preparative HPLC on a Waters X-Bridge Prep Shield RP18 (19×100 mm, 5 µm) column or a Phenomenex Gemini C18 (21.2×250 mm, 10 µm) column, using a Waters FractionLynx Autopurification System equipped with a 996 Waters PDA detector and a Micromass mod. ZQ, single quadrupole mass spectrometer, electron spray ionization, positive mode. Mobile phase A was water 0.05% NH3/acetonitrile 95:5, and Mobile phase B was acetonitrile. Gradient from 50 to 90% B in 8 min or 15 min. Flow rate 20 ml/min.

$^1$H-NMR spectrometry was performed on a Bruker AVANCE 400 MHz single bay instrument with gradients. It is equipped with a QNP probe (interchangeable 4 nuclei probe—$^1$H, 13C, 19F and 31P) (NMR method 1) or on a Mercury VX 400 operating at 400.45 MHz equipped with a 5 mm double resonance probe [1H (15N-31P) ID_PFG Varian] (NMR method 2).

The compounds of formula (I), having an asymmetric carbon atom and obtained as racemic mixture, were resolved by HPLC separation on chiral columns. In particular, for example, preparative columns CHIRALPACK® AD, CHIRALPACK® AS, CHIRALCELL® OJ can be used.

As formerly indicated, several compounds of formula (I) of the invention have been synthesized, according to solution chemistry techniques.

In this respect, some compounds thus prepared have been conveniently and unambiguously identified, as per the coding system of tables III together with HPLC retention time (methods 1, 2 and 3) and mass.

Each code, which identifies a single specific compound of formula (I), consists of three units A-M-B.

A represents any substituent R$_2$—[see formula (I)] and is attached in position 3 of the 6,7-dihydroimidazo[1,5-a]pyrazin-8(5H)-one moiety; non-limiting examples of A groups are represented in the following table I.

B represents any substituent R$_1$—[see formula (I)] and is attached to the rest of the 6,7-dihydroimidazo[1,5-a]pyrazin-8(5H)-one moiety through the carbon atom of the carbonyl group so as to get 6,7-dihydroimidazo[1,5-a]pyrazin-8(5H)-one derivatives; non-limiting examples of B groups are represented in the following table II.

M refers to the central core of the divalent 6,7-dihydroimidazo[1,5-a]pyrazin-8(5H)-one moiety being substituted in position 3 by groups A and at the carbonyl group by groups B, substantially as follows:

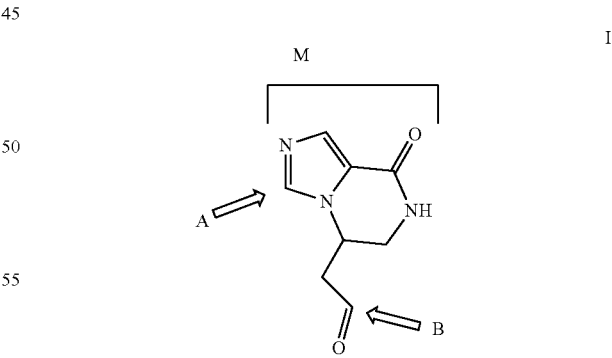

I

For ease of reference, each A or B groups of tables I and II has been identified with the proper chemical formula also indicating the point of attachment with the rest of the molecule M.

Just as an example, the compound A3-M-B3 of table III (entry 27) represents an 6,7-dihydroimidazo[1,5-a]pyrazin-8 (5H)-one M, being substituted at 3-position by the group A3 and by the group B3 through the carbonyl group, as follows:

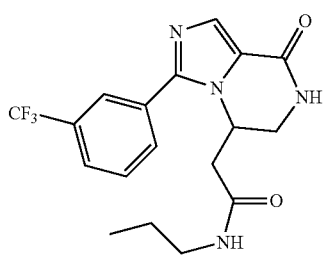

A3-M-B3

TABLE I

A groups

| Fragment | CODE | Fragment | CODE |
|---|---|---|---|
| 2-methoxyphenyl-M | A1 | 2-nitrophenyl-M | A9 |
| phenyl-M | A2 | 3-thienyl-M | A10 |
| 3-(trifluoromethyl)phenyl-M | A3 | 2-pyridyl-M | A11 |
| 2-cyanophenyl-M | A4 | 2-fluorophenyl-M | A12 |
| 4-nitrophenyl-M | A5 | 2-methylphenyl-M | A13 |
| 4-methoxyphenyl-M | A6 | 4-acetylphenyl-M | A14 |
| 3-methoxyphenyl-M | A7 | H—M | A15 |
| 3-methylphenyl-M | A8 | CH$_3$—M | A16 |

TABLE I-continued

A groups

| Fragment | CODE | Fragment | CODE |
|---|---|---|---|
| n-propyl-M | A17 | benzyl-M | A18 |

TABLE II

B groups

| Fragment | CODE | Fragment | CODE |
|---|---|---|---|
| ethoxy-M | B1 | dimethylamino-M | B8 |
| 4-methoxybenzylamino-M | B2 | cyclohexylamino-M | B9 |
| n-propylamino-M | B3 | cyclopropylamino-M | B10 |
| 2,6-diethylphenylamino-M | B4 | methoxy-M | B11 |
| isopropylamino-M | B5 | HO—M | B12 |
| isobutylamino-M | B6 | H$_2$N—M | B13 |
| tert-butylamino-M | B7 | methylamino-M | B14 |
| N-methyl-N-(2-hydroxyethyl)amino-M | B15 | 4-ethylpiperazin-1-yl-M | B24 |
| 3,5-dimethylpiperidin-1-yl-M | B16 | 2-methylphenylamino-M | B25 |
| 4-methylpiperazin-1-yl-M | B17 | 3-methylphenylamino-M | B26 |

TABLE II-continued

| B groups | | | |
|---|---|---|---|
| Fragment | CODE | Fragment | CODE |
| (cyclopentyl-NH-M) | B18 | (3-Cl-phenyl-NH-M) | B27 |
| (3-F-phenyl-NH-M) | B19 | (3,4-dimethylphenyl-NH-M) | B28 |
| (azepane-N-M) | B20 | (ethyl-NH-M) | B29 |
| (4-F-phenyl-NH-M) | B21 | (thiomorpholine-N-M) | B30 |
| (pyrrolidine-N-M) | B22 | (morpholine-N-M) | B31 |
| (butyl-NH-M) | B23 | (2-F-phenyl-NH-M) | B32 |

Preparation of 3H-imidazole-4-carboxylic acid (III)

Method A:

A mixture of 1H-Imidazole-4,5-dicarboxylic acid (II) (24.7 g, 158.23 mmol) in N-methylpyrrolidinone (198 mL) was heated at 160° C. for 23 hours under nitrogen. Then, the reaction mass was cooled to +4° C. and aged for 48 hours. The solids were collected by filtration, washed with N-methylpyrrolidinone (50 mL) and methyl tert-butyl ether (100 mL) and finally vacuum-dried at 50° C. to afford the title product 3H-Imidazole-4-carboxylic acid (III) as an off-white solid (17.74 g, 75.6% yield) m.p. 288-290° C.

LCMS (HPLC Method 4): m/z 113 [M+H]$^+$ at r.t. 0.72 min. $^1$H NMR (401 MHz, DMSO-d$_6$) δ ppm: 7.68 (s, 1H) 7.77 (s, 1H).

Method B:

In a sealed vial a suspension of 1H-imidazole-4,5-dicarboxylic acid II (1 g, 6.4 mmol) in dry DMA (10 ml) was heated under microwaves irradiation at 165° C. for 1 hour. The procedure was repeated for 5 times to avoid product decomposition occurring with continuous heating. During each run the vial was opened to leak the CO$_2$ produced by the reaction. The reaction mixture was then allowed to warm-up to room temperature and the precipitation of part of the desired product III was observed. The solvent was evaporated under reduced pressure and the crude solid was triturated with dry methyl t-butyl-ether obtaining 3H-Imidazole-4-carboxylic acid as an off-white solid in quantitative yield.

LCMS (HPLC Method 4): m/z 113 [M+H]$^+$ at r.t. 0.72 min. $^1$H NMR (401 MHz, DMSO-d$_6$) δ ppm: 7.68 (s, 1H) 7.77 (s, 1H).

Example 1

(8-oxo-5,6,7,8-tetrahydro-imidazo[1,5-a]pyrazin-5-yl)-acetic acid ethyl ester (I, A15-M-B1, R$_2$=H, R$_1$=—OCH$_2$CH$_3$)

3H-Imidazole-4-carboxylic acid (0.50 g, 4.46 mmol) (III) was suspended in dry tetrahydrofuran (34 mL) and hydrogen chloride (2 N ether solution, 6 mL, 12 mmol) was added. The mixture was stirred for 1 h at room temperature. To the suspension were added dry DMF (0.52 mL, 6.70 mmol) and thionyl chloride (3.26 mL, 44.70 mmol) and the mixture stirred under reflux overnight and concentrated under reduced pressure. To the pale yellow residue were added pyridine (50 mL) and ethyl (2E)-4-aminobut-2-enoate trifluoroacetate (IV) (2.17 g, 8.92 mmol) and the reaction mixture stirred under reflux for 5 h. The solvents were evaporated under reduced pressure, obtaining an oil which was dissolved in a mixture of saturated aqueous hydrogencarbonate solution (15 mL) and tetrahydrofuran (10 mL) and stirred for 2 h at room temperature.

The solvent was evaporated under vacuum and the residue was taken-up in dichloromethane, dried over anhydrous sodium sulfate and filtered. The filtrate was concentrated and the residue purified by silica gel flash chromatography (DCM/MeOH 9:1). The purification afforded a brown solid that was recrystallized in dichloromethane and anhydrous diethyl ether. The suspension obtained standing overnight was filtered obtaining the title compound as a white solid (0.56 g, 56% yield).

LCMS (HPLC Method 2): m/z 224 [M+H]$^+$ at r.t. 2.66 min. $^1$H NMR (401 MHz, DMSO-d$_6$) δ ppm: 1.18 (t, J=7.08 Hz, 2H) 2.90 (d, J=6.84 Hz, 1H) 3.34-3.40 (m, 1H) 3.66 (ddd, J=13.24, 4.27, 2.01 Hz, 1H) 4.10 (q, J=7.08 Hz, 1H) 4.79 (tt, J=6.73, 4.50 Hz, 1H) 7.45 (d, J=0.61 Hz, 1H) 7.81 (s, 1H) 7.85 (br. s., 1H)

Example 2

A2-M-B1

In a microwave sealed tube filled with argon, a mixture of 8-oxo-5,6,7,8-tetrahydro-imidazo[1,5-a]pyrazin-5-yl)-acetic acid ethyl ester (I, R$_2$=H, R$_1$=—OCH$_2$CH$_3$) (35 mg, 0.16 mmol), Pd(OAc)$_2$ (5 mmol %), CuI (60 mg, 0.32 mmol) and an aryl halide wherein R$_2$ corresponds to the fragment A2 of table I (0.48 mmol) in dry degassed DMF (0.7 mL, 0.23 M relative to I) was stirred at 160° C. for 3 h, under an argon atmosphere. After cooling to room temperature, the reaction mixture was diluted with MeOH (1 mL), filtered through Stratospheres™ SPE PL-thiol MP SPE tube (washed with MeOH) and the filtrate evaporated under vacuum. The residue was purified by flash chromatography (DCM/MeOH 9:1), to obtain the title compound A2-M-B1 (0.041 g, 80% yield).

LCMS (HPLC Method 2): m/z 300 [M+H]$^+$ at r.t. 4.31 min. $^1$H NMR (DMSO-d$_6$) δ ppm: 7.93 (d, J=4.6 Hz, 1H), 7.76 (dd, J=7.6, 1.7 Hz, 2H), 7.62 (s, 1H), 7.44-7.57 (m, 3H), 5.02-5.18

(m, J=4.2 Hz, 1H), 3.82-3.95 (m, 2H), 3.76 (dq, J=10.8, 7.1 Hz, 1H), 2.80 (dd, J=15.3, 8.3 Hz, 1H), 1.05 (t, J=7.1 Hz, 3H)

Example 3

A2-M-B12

A solution of A2-M-B1 (0.032 g, 0.117 mmol) and lithium hydroxide monohydrate (0.005 g, 0.214 mmol) in a mixture of THF-$H_2O$ (1:1, 0.1 M relative to A2-M-B1) was stirred at room temperature for 30 minutes. The reaction mixture was acidified with $HCl_{(conc)}$ until pH<1 and concentrated under reduced pressure obtaining the title compound A2-M-B12 as a brown solid.

Example 4

A2-M-B2

To a suspension of derivative A2-M-B12 (0.104 mmol) in dry DCM (2.0 mL, 0.05 M), EDC (0.030 g, 0.156 mmol), DHBTOH (0.025 g, 0.156 mmol), pyridine (0.025 mL, 0.312 mmol) and 4-methoxybenzilamine (0.027 mL, 0.208 mmol) were added and the reaction mixture was stirred at room temperature for 36 h. The solvent was evaporated and the residue was taken-up with water and extracted with EtOAc (2 times). The combined organic layers were dried over $Na_2SO_4$, the solvent was evaporated under vacuum and the residue purified by RP-HPLC to obtain the title compound A2-M-B2 as solid (0.020 g, 50% yield).

LCMS (HPLC Method 2): m/z 391 [M+H]$^+$ at r.t. 4.34 min. $^1$H NMR (DMSO-$d_6$) δ ppm: 8.42 (t, J=5.7 Hz, 1H), 7.92 (d, J=4.9 Hz, 1H), 7.72-7.83 (m, 2H), 7.60 (s, 1H), 7.47-7.54 (m, 3H), 7.05-7.15 (m, 2H), 6.80-6.95 (m, 2H), 5.03-5.13 (m, 1H), 4.02-4.18 (m, 2H), 3.83 (dd, J=13.4, 3.7 Hz, 1H), 3.71-3.74 (m, 3H), 2.78 (dd, J=15.1, 10.0 Hz, 1H).

Example 5

A3-M-B2

To a suspension of derivative A3-M-B12 (0.117 mmol) in a mixture of dry dioxane-acetonitrile 1:1 (1.17 mL, 0.1 M), DIEA (0.060 mL, 3.50 mmol) and TFFH (0.040 g, 0.152 mmol) were added and the reaction mixture was vigorously stirred for 1 h at room temperature. The obtained suspension became yellow during the reaction. Propylamine (0.020 mL, 0.24 mmol) and lutidine (0.021 mL, 0.176 mmol) were added and the reaction mixture stirred at 60° C. for 3 h. The solvent was evaporated and the residue was taken-up with water and extracted with DCM (1 mL, 2 times) using Alltech™ separator tubes. The combined organic layers were dried over $Na_2SO_4$, the solvent was concentrated under vacuum to half the volume and the precipitate isolated by filtration to obtain the title compound A3-M-B2 as a white solid (0.019 g, 52% yield).

LCMS (HPLC Method 2): m/z 459 [M+H]$^+$ at r.t. 5.09 min. $^1$H NMR (DMSO-$d_6$) δ ppm: 8.09 (d, J=7.8 Hz, 1H), 8.06 (s, 1H), 7.96 (d, J=5.0 Hz, 1H), 7.89 (t, J=4.3 Hz, 1H), 7.84 (d, J=8.2 Hz, 1H), 7.69-7.79 (m, 1H), 7.64 (s, 1H), 5.12 (t, J=8.4 Hz, 1H), 3.81-3.93 (m, 1H), 3.34 (br. s., 1H), 2.77-2.85 (m, 2H), 2.62-2.69 (m, 1H), 2.36 (d, J=14.9 Hz, 1H), 1.23-1.34 (m, 1H), 0.77 (t, J=7.4 Hz, 1H).

Example 6

(8-Oxo-5,6,7,8-tetrahydro-imidazo[1,5-a]pyrazin-5-yl)-acetic carboxylic acid (I, A15-M-B12, $R_1$=—OH, $R_2$=H)

Lithium hydroxide monohydrate (0.055 g, 2.33 mmol) was added to a solution of (8-oxo-5,6,7,8-tetrahydro-imidazo[1,5-a]pyrazin-5-yl)-acetic acid ethyl ester (I, $R_1$=—$OCH_2CH_3$, $R_2$=H) (0.260 g, 1.16 mmol) in a mixture of THF-$H_2O$ (1:1, 22 mL, 0.05 M relative to I) and the reaction mixture was stirred at room temperature for 30 min. The reaction mixture was acidified with $HCl_{(conc)}$ until pH<1 and it was concentrated under reduced pressure obtaining (8-oxo-5,6,7,8-tetrahydro-imidazo[1,5-a]pyrazin-5-yl)-acetic carboxylic acid hydrochloride salt (I, $R_1$=$R_2$=H) as a brown solid (0.268 g, 100% yield).

LCMS (HPLC Method 4): m/z 196 [M+H]$^+$ at r.t. 0.8 min. $^1$H NMR (DMSO-$d_6$) δ ppm: 12.73 (br. s., 1H), 8.69 (br. s., 1H), 8.28 (br. s., 1H), 7.97 (br. s., 1H), 4.88 (quin, J=5.5 Hz, 1H), 3.73 (ddd, J=13.3, 3.6, 2.4 Hz, 1H), 3.46 (dt, J=13.3, 4.4 Hz, 1H), 2.94-3.02 (m, 1H), 2.85-2.93 (m, 1H).

Example 7

A15-M-B9

To a suspension of (8-oxo-5,6,7,8-tetrahydro-imidazo[1,5-a]pyrazin-5-yl)-acetic carboxylic acid hydrochloride 1 (0.030 g, 0.153 mmol) in a mixture of dry DCM-dry DMF (9:1; 0.05 M), EDC (0.044 g, 0.230 mmol), DHBTOH (0.037 g, 0.230 mmol), pyridine (0.037 mL, 0.459 mmol) and cyclohexylamine (0.035 mL, 0.306 mmol) were added and the reaction mixture was stirred at room temperature for 36 h. The solvent was evaporated and the residue taken-up with water and the excess of DHBTOH was filtered off. The aqueous layer was evaporated under vacuum and the residue purified by HPLC to obtain the title compound A15-M-B9 as white solid (0.020 g, 48% yield).

LCMS (HPLC Method 2): m/z 277 [M+H]$^+$ at r.t. 3.87 min. $^1$H NMR (DMSO-$d_6$) δ ppm: 7.83 (br. s., 2H), 7.66 (d, J=0.6 Hz, 1H), 7.43 (d, J=0.7 Hz, 1H), 4.69-4.83 (m, 1H), 3.59-3.69 (m, 1H), 3.51 (br. s., 1H), 3.27-3.37 (m, 1H), 2.63-2.72 (m, 1H), 2.50-2.61 (m, 1H), 1.46-1.75 (m, 4H), 1.01-1.32 (m, 6H).

Example 8

Operating as described in the previous Examples, the following compounds were prepared:

TABLE III

| Entry | Compound | HPLC Method | HPLC r.t. (min) | [M + H]+ |
|---|---|---|---|---|
| 1 | A15-M-B1 | 2 | 2.66 | 224 |
| 2 | A1-M-B1 | 2 | 3.21 | 330 |
| 3 | A2-M-B1 | 2 | 4.31 | 300 |
| 4 | A2-M-B2 | 2 | 4.34 | 391 |
| 5 | A3-M-B1 | 2 | 5.13 | 368 |
| 6 | A3-M-B2 | 2 | 5.09 | 459 |
| 7 | A4-M-B1 | 2 | 3.87 | 325 |
| 8 | A5-M-B1 | 2 | 4.39 | 345 |
| 9 | A6-M-B1 | 2 | 4.29 | 330 |
| 10 | A7-M-B1 | 2 | 4.37 | 330 |
| 11 | A8-M-B1 | 2 | 4.58 | 314 |
| 12 | A10-M-B1 | 2 | 4.12 | 306 |
| 13 | A4-M-B2 | 2 | 4.29 | 416 |

TABLE III-continued

| Entry | Compound | HPLC Method | HPLC r.t. (min) | [M + H]+ |
|---|---|---|---|---|
| 14 | A9-M-B1 | 2 | 4.66 | 345 |
| 15 | A6-M-B2 | 2 | 4.54 | 421 |
| 16 | A7-M-B2 | 2 | 4.61 | 421 |
| 17 | A15-M-B12 | 4 | 0.8 | 196 |
| 18 | A10-M-B2 | 2 | 4.45 | 397 |
| 19 | A15-M-B3 | 2 | 3.44 | 237 |
| 20 | A15-M-B4 | 2 | 4.32 | 327 |
| 21 | A11-M-B1 | 2 | 3.23 | 301 |
| 22 | A1-M-B1 | 2 | 4.06 | 330 |
| 23 | A9-M-B2 | 2 | 4.85 | 436 |
| 24 | A15-M-B1 | 2 | 3.44 | 224 |
| 25 | A3-M-B11 | 2 | 4.34 | 354 |
| 26 | A2-M-B11 | 2 | 3.09 | 286 |
| 27 | A3-M-B3 | 2 | 4.66 | 381 |
| 28 | A15-M-B13 | 5 | 0.368 | 195 |
| 29 | A15-M-B14 | 5 | 0.677 | 209 |
| 30 | A15-M-B5 | 2 | 3.37 | 237 |
| 31 | A15-M-B6 | 2 | 3.87 | 251 |
| 32 | A15-M-B7 | 2 | 3.92 | 251 |
| 33 | A15-M-B8 | 2 | 3.18 | 223 |
| 34 | A15-M-B15 | 5 | 0.669 | 253 |
| 35 | A15-M-B9 | 2 | 3.87 | 277 |
| 36 | A15-M-B10 | 2 | 3.03 | 235 |
| 37 | A12-M-B3 | 1 | 2.05 | 331 |
| 38 | A12-M-B8 | 1 | 1.8 | 317 |
| 39 | A12-M-B16 | 1 | 2.99 | 385 |
| 40 | A2-M-B17 | 1 | 1.37 | 354 |
| 41 | A2-M-B5 | 1 | 1.85 | 313 |
| 42 | A2-M-B18 | 1 | 2.24 | 339 |
| 43 | A2-M-B19 | 1 | 2.75 | 365 |
| 44 | A2-M-B10 | 1 | 1.68 | 311 |
| 45 | A2-M-B20 | 1 | 2.41 | 353 |
| 46 | A2-M-B21 | 1 | 2.64 | 365 |
| 47 | A2-M-B22 | 1 | 1.82 | 325 |
| 48 | A2-M-B23 | 1 | 2.28 | 327 |
| 49 | A13-M-B3 | 1 | 2.08 | 327 |
| 50 | A13-M-B16 | 1 | 3.12 | 381 |
| 51 | A13-M-B5 | 1 | 2.04 | 327 |
| 52 | A13-M-B24 | 1 | 1.46 | 382 |
| 53 | A13-M-B14 | 1 | 1.62 | 299 |
| 54 | A13-M-B25 | 1 | 2.69 | 375 |
| 55 | A13-M-B26 | 1 | 3.02 | 375 |
| 56 | A13-M-B27 | 1 | 3.3 | 395 |
| 57 | A13-M-B28 | 1 | 3.26 | 389 |
| 58 | A13-M-B29 | 1 | 1.81 | 313 |
| 59 | A14-M-B8 | 1 | 1.74 | 341 |
| 60 | A14-M-B16 | 1 | 2.81 | 409 |
| 61 | A14-M-B30 | 1 | 2.02 | 399 |
| 62 | A14-M-B31 | 1 | 1.76 | 383 |
| 63 | A14-M-B26 | 1 | 2.64 | 403 |
| 64 | A14-M-B9 | 1 | 2.57 | 395 |
| 65 | A14-M-B18 | 1 | 2.26 | 381 |
| 66 | A14-M-B32 | 1 | 2.29 | 407 |
| 67 | A8-M-B2 | 4 | 6.89 | 405 |
| 68 | A10-M-B12 | 4 | 2.495 | 278 |

The invention claimed is:

1. A compound of the formula (I):

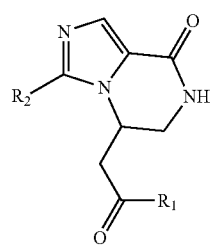

I wherein:

$R_1$ is $-NR_3R_4$ or $-OR_3$;

$R_2$ is a hydrogen atom or an optionally substituted group selected from straight or branched $C_1$-$C_6$ alkyl, aryl, heteroaryl, aryl $C_1$-$C_6$ alkyl and heteroaryl $C_1$-$C_6$ alkyl;

$R_3$ and $R_4$, the same or different, are each independently hydrogen atom or an optionally substituted group selected from straight or branched $C_1$-$C_6$ alkyl, $C_2$-$C_6$ alkenyl, $C_2$-$C_6$ alkynyl, $C_3$-$C_6$ cycloalkyl, cycloalkyl $C_1$-$C_6$ alkyl, heterocyclyl, heterocyclyl $C_1$-$C_6$ alkyl, aryl, aryl $C_1$-$C_6$ alkyl, heteroaryl and heteroaryl $C_1$-$C_6$ alkyl, or $R_3$ and $R_4$, taken together with the nitrogen atom to which they are bonded, may form an optionally substituted 3 to 7 membered heterocyclyl or heteroaryl ring, optionally containing one additional heteroatom or heteroatomic group selected from S, O, N and NH; or a pharmaceutically acceptable salt thereof, wherein the optionally substituted group of $R_2$, $R_3$ and $R_4$ is substituted in any of its free positions by 1 to 6 groups, selected from the groups consisting of: halogen, nitro, oxo groups (=O), carboxy, cyano, $C_1$-$C_6$ alkyl, polyfluorinated alkyl, $C_2$-$C_6$ alkenyl, $C_2$-$C_6$ alkynyl, $C_3$-$C_6$ cycloalkyl, heterocyclyl, aryl, heteroaryl; amino groups and derivatives thereof; carbonylamino groups and derivatives thereof; hydroxy groups and derivatives thereof; carbonyl groups and derivatives thereof; and sulfurated derivatives, wherein when $R_1$ is $-NR_3R_4$, only one of $R_3$ and $R_4$ are hydrogen and when $R_1$ is $-OR_3$, $R_3$ is not hydrogen.

2. A compound of formula (I) according to claim 1 wherein $R_1$ is $-NH_2$ or $NHR_3$ and $R_3$ is a straight or branched $C_1$-$C_6$ alkyl or $C_2$-$C_6$ alkenyl group or it is an optionally substituted aryl or arylalkyl group, wherein the optionally substituted aryl or arlyalkyl of $R_3$ is substituted in any of its free positions by 1 to 6 groups, selected from the groups consisting of: halogen, nitro, oxo groups (=O), carboxy, cyano, $C_1$-$C_6$ alkyl, polyfluorinated alkyl, $C_2$-$C_6$ alkenyl, $C_2$-$C_6$ alkynyl, $C_3$-$C_6$ cycloalkyl, heterocyclyl, aryl, heteroaryl; amino groups and derivatives thereof; carbonylamino groups and derivatives thereof; hydroxy groups and derivatives thereof; carbonyl groups and derivatives thereof; and sulfurated derivatives.

3. A compound of formula (I) according to claim 1 wherein $R_2$ is hydrogen or an optionally substituted aryl or heteroaryl group, wherein the optionally substituted aryl or heteroaryl of $R_2$ is substituted in any of its free positions by 1 to 6 groups, selected from the groups consisting of: halogen, nitro, oxo groups (=O), carboxy, cyano, $C_1$-$C_6$ alkyl, polyfluorinated alkyl, $C_2$-$C_6$ alkenyl, $C_2$-$C_6$ alkynyl, $C_3$-$C_6$ cycloalkyl, heterocyclyl, aryl, heteroaryl; amino groups and derivatives thereof; carbonylamino groups and derivatives thereof; hydroxy groups and derivatives thereof; carbonyl groups and derivatives thereof; and sulfurated derivatives.

4. A compound of formula (I) according to claim 1 wherein $R_2$ is a fragment denoted by any of codes A1-A18 and R1 is a fragment denoted by any of codes B1-B32:

| Fragment | CODE | Fragment | CODE |
|---|---|---|---|
|  | A1 |  | A9 |

| Fragment | CODE | Fragment | CODE |
|---|---|---|---|
| phenyl-M | A2 | 3-thienyl-M | A10 |
| 3-(trifluoromethyl)phenyl-M | A3 | pyridin-2-yl-M | A11 |
| 2-cyanophenyl (NC, N)-M | A4 | 2-fluorophenyl-M | A12 |
| 4-nitrophenyl-M | A5 | 2-methylphenyl-M | A13 |
| 4-methoxyphenyl-M | A6 | 4-acetylphenyl-M | A14 |
| 3-methoxyphenyl-M | A7 | H—M | A15 |
| 3-methylphenyl-M | A8 | CH₃-M | A16 |
| propyl-M | A17 | benzyl-M | A18 |
| ethoxy-M (EtO-M) | B1 | (CH₃)₂N-M | B8 |
| 4-methoxybenzyl-NH-M | B2 | cyclohexyl-NH-M | B9 |
| propyl-NH-M | B3 | cyclopropyl-NH-M | B10 |
| 2,6-diethylphenyl-NH-M | B4 | methoxy-M (MeO-M) | B11 |
| isopropyl-NH-M | B5 | HO—M | B12 |
| isobutyl-NH-M | B6 | H₂N—M | B13 |
| tert-butyl-NH-M | B7 | methyl-NH-M | B14 |
| N-methyl-N-(2-hydroxyethyl)-M | B15 | 4-ethylpiperazin-1-yl-M | B24 |
| 3,5-dimethylpiperidin-1-yl-M | B16 | 2-methylphenyl-NH-M | B25 |
| 4-methylpiperazin-1-yl-M | B17 | 3-methylphenyl-NH-M | B26 |
| cyclopentyl-NH-M | B18 | 3-chlorophenyl-NH-M | B27 |
| 3-fluorophenyl-NH-M | B19 | 3,4-dimethylphenyl-NH-M | B28 |
| azepan-1-yl-M | B20 | ethyl-NH-M | B29 |

| Fragment | CODE | Fragment | CODE |
|---|---|---|---|
| ![B21 structure] | B21 | ![B30 structure] | B30 |
| ![B22 structure] | B22 | ![B31 structure] | B31 |
| ![B23 structure] | B23 | ![B32 structure] | B32 |

5. A process for preparing a compound of the formula (I) or the pharmaceutically acceptable salts thereof, as defined in claim 1, which process comprises:

a) decarboxylating a compound of formula (II):

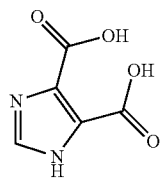

II b) reacting the resultant compound of formula (III):

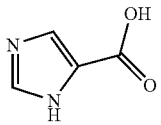

III with a compound of formula (IV) or a salt thereof:

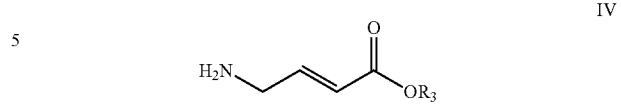

IV wherein $R_3$ is a $C_1$-$C_6$ alkyl group, so as to obtain a compound of formula (I):

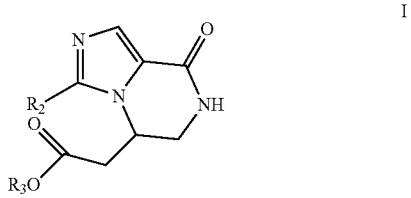

I wherein $R_3$ is a $C_1$-$C_6$ alkyl group and $R_2$ is hydrogen, or a pharmaceutically acceptable salt thereof and, if necessary or desired, performing one or more of the following additional steps:

separating the compound of formula (I) into the single isomers;

converting a compound of formula (I) into a different compound of formula (I) by introduction on the imidazole moiety of a $R_2$ group as defined in claim 1 but different from hydrogen;

converting a compound of formula (I) into a different compound of formula (I) by replacing the group —$OR_3$ with a different group $R_1$ as defined in claim 1;

converting a compound of formula (I) into a pharmaceutically acceptable salt or converting a salt into the free compound (I).

6. A pharmaceutical composition comprising a therapeutically effective amount of a compound of formula (I), as defined in claim 1, and at least one pharmaceutically acceptable carrier and/or diluent.

7. A pharmaceutical composition according to claim 6 further comprising one or more chemotherapeutic agents.

8. A product comprising a compound of formula (I) as defined in claim 1 or a pharmaceutical composition thereof comprising said compound and at least one pharmaceutically acceptable carrier and/or diluent, and one or more chemotherapeutic agents, as a combined preparation for simultaneous, separate or sequential use in anticancer therapy.

* * * * *